United States Patent
Maxwell et al.

(10) Patent No.: US 7,347,985 B2
(45) Date of Patent: *Mar. 25, 2008

(54) BREATH FRESHENING AND ORAL CLEANSING PRODUCT WITH MAGNOLIA BARK EXTRACT

(75) Inventors: James Roy Maxwell, Chicago, IL (US); Michael J. Greenberg, Northbrook, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/606,671

(22) Filed: Jun. 25, 2003

(65) Prior Publication Data

US 2004/0081713 A1    Apr. 29, 2004

Related U.S. Application Data

(60) Provisional application No. 60/319,346, filed on Jun. 25, 2002.

(51) Int. Cl.
*A61K 8/97* (2006.01)
*A61K 6/00* (2006.01)

(52) U.S. Cl. ............ 424/58; 424/49; 424/725; 424/435; 424/439; 426/615

(58) Field of Classification Search ....... 424/725, 424/400, 439, 49, 58, 435; 426/615
See application file for complete search history.

(56) References Cited

U.S. PATENT DOCUMENTS

| | | | |
|---|---|---|---|
| 1,056,212 A | 3/1913 | Puetzer et al. | |
| 3,452,138 A | 6/1969 | Granatek et al. | |
| 4,547,361 A | 10/1985 | Steltenkamp et al. | |
| 4,562,020 A | 12/1985 | Hijiya et al. | |
| 4,568,560 A | 2/1986 | Schobel | |
| 4,820,544 A | 4/1989 | Barcelon et al. | |
| 4,971,806 A | 11/1990 | Cherukuri et al. | |
| 5,149,521 A | 9/1992 | Hirose et al. | |
| 5,487,902 A | 1/1996 | Andersen et al. | |
| 5,939,050 A | 8/1999 | Iyer et al. | |
| 5,948,430 A | 9/1999 | Zerbe et al. | |
| 6,177,096 B1 | 1/2001 | Zerbe et al. | |
| 6,248,309 B1 | 6/2001 | Iyer et al. | |
| 6,280,751 B1 | 8/2001 | Fletcher et al. | |
| 6,284,264 B1 | 9/2001 | Zerbe et al. | |
| 6,495,512 B1 | 12/2002 | White et al. | |
| 6,500,406 B1 | 12/2002 | Rajaiah et al. | |
| 6,500,409 B1 | 12/2002 | Scherl et al. | |
| 6,552,024 B1 | 4/2003 | Chen et al. | |
| 6,582,735 B2 | 6/2003 | Stogniew et al. | |
| 6,596,298 B2 | 7/2003 | Leung et al. | |
| 6,656,493 B2* | 12/2003 | Dzija et al. | 424/439 |
| 6,703,000 B2 | 3/2004 | Ning et al. | |
| 6,740,332 B2* | 5/2004 | Zyck et al. | 424/435 |
| 6,923,981 B2 | 8/2005 | Leung et al. | |
| 2001/0018043 A1 | 8/2001 | Henning et al. | |
| 2001/0022964 A1 | 9/2001 | Leung et al. | |
| 2002/0131990 A1 | 9/2002 | Barkalow et al. | |
| 2003/0007997 A1 | 1/2003 | Lawlor | |
| 2003/0008062 A1 | 1/2003 | Day et al. | |
| 2003/0224090 A1 | 12/2003 | Pearce et al. | |
| 2004/0086546 A1* | 5/2004 | Maxwell et al. | 424/439 |
| 2004/0253189 A1* | 12/2004 | Maxwell et al. | 424/49 |
| 2004/0253190 A1* | 12/2004 | Maxwell et al. | 424/49 |
| 2004/0253191 A1* | 12/2004 | Maxwell et al. | 424/49 |
| 2004/0253192 A1* | 12/2004 | Maxwell et al. | 424/49 |
| 2004/0253278 A1* | 12/2004 | Maxwell et al. | 424/400 |
| 2004/0258733 A1* | 12/2004 | Maxwell et al. | 424/439 |
| 2005/0013902 A1 | 1/2005 | Pearce | |

FOREIGN PATENT DOCUMENTS

| | | |
|---|---|---|
| CN | 1094895 A | 11/1994 |
| CN | 1096694 A | 12/1994 |
| CN | 1096699 A | 12/1994 |
| CN | 1115212 A | 1/1996 |
| CN | 1127136 A | 7/1996 |
| CN | 1141194 A | 1/1997 |
| CN | 1073410 C | 10/2001 |
| GB | 1311060 | 3/1973 |

(Continued)

OTHER PUBLICATIONS

Al/Zuhair et al., *Pharmacological Studies of Cardamon Oil in Animals*. Pharmacological Research, vol. 34, No. 1 /2, 1996.

(Continued)

*Primary Examiner*—Ruth A Davis
(74) *Attorney, Agent, or Firm*—Brinks Hofer Gilson & Lione

(57) ABSTRACT

A pullulan-free edible film composition for oral cleansing, breath freshening, and anti-microbial benefits includes a film forming agent and Magnolia Bark Extract. In a treatment process, an effective amount of Magnolia Bark Extract is delivered to the oral cavity by the edible film for convenient oral cleansing and breath freshening benefits. A method of making the pullulan-free edible film composition includes forming an aqueous solution of film forming agents and Magnolia Bark Extract and drying the aqueous solution to form a dry edible film.

73 Claims, No Drawings

FOREIGN PATENT DOCUMENTS

| | | |
|---|---|---|
| JP | 57085319 A * | 5/1982 |
| JP | SHO-84-175422 | 10/1984 |
| KR | 1996-0007923 | 6/1996 |
| KR | 2002-0003413 | 1/2002 |
| WO | WO 93/15116 | 8/1993 |
| WO | 1094895 | 11/1994 |
| WO | WO 97/35599 | 10/1997 |
| WO | WO 99/18940 | 4/1999 |
| WO | WO 99/51093 | 10/1999 |
| WO | WO 00/42992 A2 | 7/2000 |
| WO | WO 01/82922 | 11/2001 |
| WO | WO 01/85116 A2 * | 11/2001 |
| WO | WO 02/43657 A2 * | 6/2002 |
| WO | WO 02/091848 A1 | 11/2002 |
| WO | WO 02091848 | 11/2002 |

OTHER PUBLICATIONS

Supplementary Partial European Search Report for Application No. EP 032 74 2198 dated Mar. 29, 2006.

* cited by examiner

BREATH FRESHENING AND ORAL CLEANSING PRODUCT WITH MAGNOLIA BARK EXTRACT

RELATED U.S. APPLICATION

Priority is claimed to provisional patent application Ser. No. 60/319,346, filed Jun. 25, 2002.

TECHNICAL FIELD

The present invention relates, in general, to edible films and, more particularly, to pullulan-free edible film compositions containing Magnolia Bark Extract and to methods of making the film compositions.

BACKGROUND

There is considerable consumer demand for products that freshen breath and kill bacteria in the mouth. An oral product with breath freshening and bactericidal benefits is a convenient delivery for oral cleansing in the oral cavity and freshening breath.

Of course, breath freshening is a very important part of everyday life. In order to facilitate proper oral hygiene, oral cleansing and breath freshening practices should be conducted repeatedly throughout the day.

However, oral cleansing and breath freshening may be difficult or inconvenient at times, depending on the nature of the breath freshening desired and the situation in which the breath freshening must occur. Brushing, flossing, cleaning your tongue and gargling using a variety of devices and compositions are common oral care practices well-suited for the privacy of one's home. But, such devices and compositions are less convenient to use away from the home where bathroom facilities might be scarce, unavailable or unsanitary.

It is known to incorporate active agents into oral products for the purpose of providing oral benefits including breath freshening and bactericidal properties. Such systems have the advantage of providing a rapid effect and convenient delivery.

SUMMARY OF INVENTION

The present invention relates to the composition of, and methods of producing an oral product. Specifically, the present invention relates to oral products intended for bactericidal and breath freshening properties. More specifically, the present invention relates to a dentifrice, chewing gum, confection, lozenge, mouth spray or edible film containing an effective amount of Magnolia Bark Extract, by which the inventive composition effectively inactivates or kills oral bacteria and freshens breath through the consumption of the dentifrice, chewing gum, confection, lozenge, mouth spray or edible film product.

In an embodiment of the present invention, the oral product is chewing gum or any variation including but not limited to bubble gums, pellets, gum balls or sticks. Chewing gums may be coated or not coated and be of a variety of flavors, shapes and sizes.

In an embodiment of this invention, the oral product is a confectionery composition including but not limited to hard candy, chewing candy, filled candy and pressed tablets.

In another embodiment of the present invention, the oral product is a pullulan-free edible film composition that includes an effective amount of a film forming agent, and an effective amount of an antimicrobial agent wherein the antimicrobial agent comprises Magnolia Bark Extract.

In yet another embodiment of the invention, a method of oral cleansing includes applying a pullulan-free edible film to the oral cavity, where the edible film includes an effective amount of a film forming agent, and an effective amount of an antimicrobial agent where the antimicrobial agent comprises Magnolia Bark Extract.

In still another embodiment of the invention, a method of making a pullulan-free edible film includes forming an aqueous solution that includes a maltodextrin, a hydrocolloid, and a filler, adding an effective amount of an antimicrobial agent to the aqueous solution, where the antimicrobial agent comprises Magnolia Bark Extract, and drying the aqueous solution to form a dry edible film.

A further embodiment of the invention includes a treatment method for reducing the number or activity of bacteria in the oral cavity by providing an edible film composition including Magnolia Bark Extract in an amount sufficient to kill or deactivate oral bacteria, and causing a person in need of the treatment to consume the edible film composition, whereby the bacteria in the oral cavity of the person is reduced or inactivated by the treatment.

In another embodiment the oral product is a dentifrice.

DETAILED DESCRIPTION

It is known to use chewing gum, confections and thin films as a vehicle for delivering components to the oral cavity which provide oral benefits such as breath freshening and bactericidal properties. Such systems have the advantage of providing a consumer with a convenient and inexpensive method for maintaining oral health and fresh breath throughout the course of the day.

The present invention incorporates Magnolia Bark Extract as the active component for breath freshening and oral bactericidal benefits. Magnolia Bark Extract is known to have bactericidal and anti fungal properties. Magnolol and honokiol are two components in Magnolia Bark Extract with anti microbial activity.

In vitro tests were conducted with three subgingival plaque bacteria associated with oral malodor. The MIC (Minimum Inhibitory Concentrations) study protocol is as follows. Chlorhexidine was used as a positive control and sterile water was used as a negative control. Menthol and Tween 80 was used as a solvent for Magnolia Bark Extract. Ninty-six microtiter plates were used for this study. Each well contained $5 \times 10^5$ colony forming units/ml of bacteria, serially diluted agents and bacterial growth medium. All bacterial cultures were incubated at 37° C. and stationary. Bacterial growth was estimated spectrophotometrically at 660 nm, after 48 hours. The MIC for each test bacteria was defined as the minimum concentration of test compound limiting turbidity to less than 0.05 absorbance at 660 nm.

The MBC (Minimum bactericidal concentrations) were determined using the nine six-well microtiter plate serial dilutions as described above for MIC studies. Serial dilution of cultures in wells showing no visible growth were performed and 10 microliters of culture were plated in triplicate on blood agar plates. Viable colonies were scored after incubation of the plates for 48 hours at 37° C. For each test bacterium, the number of CFU/ml were determined in the initial inoculum. The MBC was defined as the lowest concentration of a test compound that killed at least 99.9% of the cells present in the initial inoculum.

The results of the studies performed to obtain minimum inhibitory concentration (MIC) and minimum bactericidal concentration (MBC) of Magnolia Bark Extract are as follows. Against *S. mutans* a Magnolia Bark extract of 90% had an MIC of 15.62 μg/ml. For *P. gingivalis*, the 90% Magnolia Bark extract had an MIC of 3.91 μg/ml, and the 65% Magnolia Bark extract had an MIC of 7.82 μg/ml. For *F. nucleatum* the 90% Magnolia Bark extract had an MIC of 3.91 μg/ml and an MBC of 7.82 μg/ml. Against the same organism, the 65% Magnolia Bark extract had an MIC and MBC of 7.82 μg/ml. chlorohexidine was the positive control and produced an MIC and MBC of 1.25 μg/ml for all three bacteria. The solvent of water with 10% methanol and 3.8% Tween 80 had no noticeable growth inhibitory effects on any of the three bacteria in the study.

It is also known that Magnolia Bark Extract is effective against *Actinobacillus actinomyecetemcomitans, Porphyromonas gingivalis, Prevotella intermedia, Micrococcus luteus,* and *Bacillus subtilis, Prevotella gingivalis, Veillonella disper, Capnocytophaga gingivalis*, periodontic microorganisms and gingival fibroblasts.

The Magnolia Bark Extract used in the present invention is obtained from Guang Zhou Masson Pharmaceutical Co., LTD, 17 2, ShuiYin Road, Guang Zhou P. R. China. The Magnolia Bark Extract is obtained in the form of a waxy paste. The Magnolia Bark Extract is dissolved with the flavor and may be warmed to dissolve prior to making the oral product.

In an embodiment, the invention comprises a treatment method for reducing the number or activity of bacteria in the oral cavity comprising the steps of providing an oral composition comprising Magnolia Bark Extract in an amount sufficient to kill or deactivate oral bacteria and causing a person in need of the treatment to consume the oral composition whereby the bacteria in the oral cavity of the person is reduced or inactivated by the treatment.

In an embodiment, the oral composition comprises additional breath freshening or oral health ingredients.

In an embodiment, the additional breath freshening or oral health ingredients comprise anti-microbial ingredients.

In an embodiment, the additional breath freshening or oral health ingredients comprise food acceptable salts of zinc or copper.

In an embodiment, the additional breath freshening or oral health ingredients comprise cooling agents.

In an embodiment, the additional breath freshening or oral health ingredients comprise pyrophosphate or polyphosphate.

In an embodiment, the oral composition is formulated to deliver at least 0.005% concentration of Magnolia Bark extract to the oral cavity.

In an embodiment, the oral composition is formulated to deliver at least 0.01% concentration of Magnolia Bark Extract to the oral cavity.

In an embodiment, the oral compositions is formulated to deliver at least 0.1% concentration of Magnolia Bark Extract to the oral cavity.

Given that Magnolia Bark extract is a hydrophobic compound, there are several methods, which may be used to enhance the release of the Magnolia Bark Extract from the oral composition. In a chewing gum product, the gum base is hydrophobic which does not facilitate the release of the Magnolia Bark Extract. In an oral composition, the Magnolia Bark Extract may be encapsulated, spray dried, formulated into a coating, and combinations thereof.

In general, a chewing gum composition typically comprises a water-soluble bulk portion, a water-insoluble chewable gum base portion and typically water-soluble flavoring agents. The waterportion dissipates with a portion of the flavoring agent over a period of time during chewing. The gum base portion is retained in the mouth throughout the chew.

In general, a chewing gum composition typically comprises a waterbulk portion, a waterchewable grams base portion and typically waterflavoring agents. The waterportion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

In a particular embodiment, the chewing gum base of the present invention contains about 20% to about 60% by weight synthetic elastomer, up to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrenecopolymers having styrene-butadiene ratios of about 1:3 to about 3:1, polyvinyl acetate having GPC weight average molecular weight of about 2,000 to about 90,000, polyisoprene, polyethylene, vinyl acetate vinyl laurate copolymer having vinyl laurate content of about 5% to about 50% by weight of the copolymer, and combinations thereof.

Preferred ranges for polyisobutylene are 50,000 to 80,000 GPC weight average molecular weight; for styrene are 1:1 to 1:3 bound styrene; for polyvinyl acetate are 10,000 to 65,000 GBC weight average molecular weight, with the higher molecular weight polyvinyl acetates typically used in bubble gum base; and for vinyl acetate laurate, a vinyl laurate content of 10.

Natural elastomers may include natural rubber, such as smoked or liquid latex and guayule, as well as natural gums, such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha beta and/or any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono and triglycerides, acetylated monoglycerides, fatty acids (e.g. stearic, palmitic, oleic and linoleic acids), and combinations thereof.

Colorants and whiteners may include FD&C dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouthfeel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide components commonly known in the chewing gum art, including but not limited to, sucrose, dextrose, maltose, dextrin, dried invert sugar, fructose, levulose, galactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, NAPM derivatives such as neotame, salts of acesulfame, altitame, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low caloric gum is desired, a low caloric bulking agent can be used. Examples of low caloric bulking agents include: polydextrose; raftilose, raftilin; fructooligosaccharides (NutraFlora); Palatinose oligosaccharide; guar gum hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion. Flavoring may include a cooling agent to enhance the flavor and perceived breath freshening of the product. Cooling agents include menthol, ethyl p-menthane carboxamide, N,2,3-trimethyl-2-isopryl-butanamide, menthyl glutarate (Flavor Extract Manufacturing Association (FEMA 4006)), menthyl succinate, menthol PG carbonate, menthol EG carbonate, menthyl lactate, menthone glyceryl ketal, menthol glyceryl ether, N-tertbutyl-p-menthane-3-carboxamide, p-menthane-3-carboxylic acid glycerol ester, methyl-2-isopryl-bicyclo (2.2.1), heptane-2-carboxamide, menthol methyl ether and combinations thereof.

In additions to the Magnolia Bark Extract of the present invention, additional active ingredients or medicaments may be added for various purposes. If the medicament or active is water soluble in the chewing gum, it preferably will include a base/emulsifier system which leads to the desired concentration of the medicament in the saliva (more hydrophilic balance). If the medicament or active is water insoluble, the chewing gum preferably includes a base/emulsifier system which leads to the desired concentration of the medicament in the saliva (more lipophilic balance).

In manufacturing the chewing gum including the active agent or ingredient, the active agent or medicament is added, preferably, early on in the mix. The smaller the amount of active ingredient used, the more necessary it becomes to preblend that particular ingredient to assume uniform distribution throughout the batch of gum. Whether a preblend is used or not, the active agent or medicament should be added within the first five minutes of mixing. For faster release, the active agent may be added late in the process.

Optionally, the chewing gum of the present invention may include additional breath freshening, anti microbial or oral health ingredients, such as food acceptable metallic salts selected from zinc and copper salts of gluconic acid, zinc and copper salts of lactic acid, zinc and copper salts of acetic acid, zinc and copper salts of citric acid and combinations thereof.

Anti-microbial essential oils and flavor components such as peppermint, methyl salicylate, thymol, eucalyptol, cinnamic aldehyde, polyphosphate, pyrophosphate and combinations thereof may be added to the gum composition.

Dental health ingredients such as fluoride salts, phosphate salts, proteolytic enzymes, lipids, anti-microbials, calcium, electrolytes, protein additives, dental abrasives and combinations thereof may also be added to the gum composition.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

Chewing gum base and chewing gum product have been manufactured conventionally using separate mixers, different mixing technologies and, often, at different factories. One reason for this is that the optimum conditions for manufacturing gum base, and for manufacturing chewing gum from gum base and other ingredients such as sweeteners and flavors, are so different that it has been impractical to integrate both tasks. Chewing gum base manufacture, on the one hand, involves the dispersive (often high shear) mixing of difficult-to-blend ingredients such as elastomer, filler, elastomer plasticizer, base softeners/emulsifiers and sometimes wax, and typically requires long mixing times. Chewing gum product manufacture, on the other hand, involves combining the gum base with more delicate ingredients such as product softeners, bulk sweeteners, high intensity sweeteners and flavoring agents using distributive (generally lower shear) mixing, for shorter periods.

The following are examples of formulations of Magnolia Bark Extract in chewing gum. The examples are not intended to exclude other variations in formulations and the present invention is not limited to these formulations.

TABLE 1

Antimicrobial Gum Formulas (% weight)

| Ingredient | Example 1 | Example 2 | Example 3 | Example 4 | Example 5 |
|---|---|---|---|---|---|
| Gum Base | 25.21 | 25.21 | 25.21 | 25.21 | 25.21 |
| Lecithin | 0.17 | 0.17 | 0.17 | 0.17 | 0.17 |
| NaHCO3 | 0.25 | 0.25 | 0.25 | 0.25 | 0.25 |
| Sorbitol | 50.86 | 49.86 | 47.86 | 45.86 | 50.36 |
| Magnolia Bark Extract | — | 1.00 | 3.00 | 5.00 | 0.50 |
| Mannitol | 4.25 | 4.25 | 4.25 | 4.25 | 4.25 |
| Lycasin/ Glycerin | 8.51 | 8.51 | 8.51 | 8.51 | 8.51 |
| Glycerin | 8.50 | 8.50 | 8.50 | 8.50 | 8.50 |
| Encapsulated Sweetener | 0.67 | 0.67 | 0.67 | 0.67 | 0.67 |
| Flavor | 1.58 | 1.58 | 1.58 | 1.58 | 1.58 |
| Total % | 100.00 | 100.00 | 100.00 | 100.00 | 100.00 |

In an embodiment of the present invention, and effective amount for anti microbial benefit of Magnolia Bark Extract is present in an edible film formulation. In an embodiment of the present invention, the amount of Magnolia Bark Extract is present in an amount up to 10% by weight of the edible film formulation. In an embodiment of the present invention, the amount of Magnolia Bark Extract is about 8% of the weight of the edible film product. In another embodiment, the Magnolia Bark Extract is present in the amount of about 5% by weight of the edible film product. Considering the potency of Magnolia Bark Extract as described in the in vitro studies above, about 1% by weight of the edible film product may also be effective in bactericidal properties.

The present invention provides edible film formulations for oral mucoadhesion and methods of using and making same. In particular, the edible films of the present invention include at least three types of film forming agents other than pullulan.

Applicants have uniquely discovered that the use of a mixture of at least three types of film forming agents, such as maltodextrins, fillers (e.g., microcrystalline cellulose (MCC)) and hydrocolloids (e.g., sodium aliginate), can be effectively utilized to prepare stand alone edible films. The edible films are composed of ingredients that are readily available, can be prepared at lower costs and display similar properties as compared to edible films composed of pullulan. In this regard, the edible films can provide a physiologically acceptable film, which is suitably adapted to adhere to oral surfaces of an oral cavity and rapidly dissolve therein.

The edible films of the present invention can be utilized to deliver or release oral care agent(s). Such agents include, anti-microbial agents and salivary stimulants to treat, for example, halitosis, dental plaque, gingivitis, xerostomia, dry mouth, like oral conditions or combinations thereof. Further, the oral care edible film can act as a breath freshener effective against malodor.

The oral cleansing and breath freshening effects of the edible film of the present invention can be achieved by entrapping the oral care agents within the oral cavity to provide extended efficacy. In this regard, the highly dissolvable edible film can act as a medium through which a pharmaceutically active oral agent can be administered via a mucous membrane of the oral cavity.

Further, the edible films can include a variety of other suitable ingredients, such as softeners, colorants, flavoring agents, emulsifiers, surfactants, thickening agents, binding agents, sweeteners, fragrances, other like ingredients or combinations thereof.

In an embodiment, the edible films preferably include a mixture of at least three types of film forming agents, such as maltodextrins, fillers and hydrocolloids. It should be appreciated that the edible film of the present invention can be composed of one or more different compounds associated with each of the at least three types of film forming agents.

In an embodiment, the maltodextrin component constitutes between about 5% to about 60% by dry weight of the edible film, preferably about 20% to about 40% by dry weight. The maltodextrin component can be processed in any suitable way.

The hydrocolloid can provide thickness and decrease brittleness of the edible films. The hydrocolloid can include any suitable type, amount and number of hydrocolloids. In an embodiment, the hydrocolloid can constitute between about 10% to about 50% by dry weight of the edible film, preferably about 20% to about 30% by dry weight. The hydrocolloid can be derived from, for example, natural seaweeds, natural seed gum, natural plant exudates, natural fiber extracts, biosynthetic gums, gelatins, biosynthetic process starch or cellulosic materials, alginates, sodium alginate, calcium alginate, carrageenans, guar gum, locust gum, tara gum, gum arabic, ghatti gum, agar gum, xanthan gum, pectin, other like hydrocolloid source material or combinations thereof.

Any suitable food-grade bulk filler can also be added to the edible film. This can reduce any slimy texture as well as provide structure to the film thereby making it more palatable. In an embodiment, the filler can constitute about 5% to about 30% by dry weight of the film, preferably about 15% to about 25% by dry weight. The filler can include, for example, microcrystalline cellulose, cellulose polymers, such as wood, magnesium and calcium carbonate, ground limestone, silicates, such as magnesium and aluminum silicate, clay, talc, titanium dioxide, mono-calcium phosphate, di-calcium phosphate, tri-calcium phosphate, other like bulk fillers or combinations thereof.

It is believed that the unique mixture of at least three film forming agents other than pullulan, for example, a maltodextrin, a hydrocolloid and a bulk filler, can provide a stand alone edible film composition which exhibits many of the same desirable properties exhibited by more expensive pullulan-based edible film. Applicants have desirably discovered that the pullulan-free edible film formulation of the present invention can exhibit, for example, clean mouth feel, clean favor and ease of manufacture similar to currently available pullulan-based films.

As previously discussed, a variety of other suitable ingredients can be added to the edible film of the present invention. For example, any suitable medicament for oral cleansing, breath freshening or the like can be added to the film formulation. The medicaments can include, for example, a pH control agent, such as urea and buffers, inorganic components for tartar or caries control, such as phosphates and fluorides, a breath freshening agent such as zing gluconate, an anti-plaque/anti-gingivitis agent, such as chlorohexidine, cetylpyridinium chloride (CPC), and triclosan, a saliva stimulating agent including, for example, food acids such as citric, lactic, maleic, succinic, ascorbic, adipic, fumaric and tartaric acids, a pharmaceutical agent, a nutraceutical agent, a vitamin, a mineral, other like medicaments or combinations thereof.

The medicaments can be delivered or released into the oral cavity for effective oral treatment, such as oral cleansing and/or breath freshening. In this regard, the film forming agent of the edible film can act to entrap the medicaments within the oral cavity thereby providing extended efficacy thereof. In doing so, it is believed that the pullulan-free edible film compositions of the present invention more uniformly release the medicament into the oral cavity for absorption via open wounds or mucous membrane in a greater manner than could be previously achieved. Moreover, it is also believed that the mixture of film forming agents of the present invention can entrap the medicament within the oral cavity for an extended period of time to prolong and enhance the effects of the medicament. In addition, by extending the contact time of the medicament within the oral cavity, the medicament is absorbed to a greater extent thereby increasing its bioavailability.

If reduced levels of film forming agents are utilized, softeners can be used to reduce the brittleness of the resulting films. The softeners, which are also known as plasticizers or plasticizing agents, generally constitute between about up to 20% by dry weight of the film, preferably about 2% to about 10% by dry weight. The softeners can include plasticizers containing, for example, sorbitol and other polyols, glycerin, polyethylene glycol, propylene glycol, hydrogenated starch hydrolysates, corn syrups, other like material or combinations thereof.

The edible film formulations of the present invention can also include colorants or coloring agents which can be used in any suitable amount to produce the desired color. Coloring agents can include, for example, natural food colors and dyes suitable for food, drug and cosmetic applications. The colorants are typically knows as FD&C dyes and lakes.

A variety of flavoring agents can also be added to the edible films. Any suitable amount and type of artificial and/or natural flavoring agents can be used in any sensorially acceptable fashion. For example, the flavor can constitute about 0.1% to about 20% by dry weight of the film, preferably about 10% to 15%. The flavoring agent can include, for example, essential oils, synthetic flavors or mixtures including but not limited to oils delivered from plants and fruits such as citrus oils, fruit essences, peppermint oil, spearmint oil, other mint oils, clove oils, oil of wintergreen, anise and the like, flavor oils with germ killing properties such as menthol, eucalyptol, thymol, like flavoring agents or combinations thereof.

The flavor can be enhanced and evenly distributed throughout the product by emulsification. Any suitable amount and type of natural and/or synthetic food grade emulsifier can be used. For example, the emulsifier can include lecithin, food-grade non-ionic emulsifiers, such as fatty acids ($C_{10}$-$C_{18}$), mono and diacyl glycerides, ox bile extract, polyglycerol esters, polyethylene sorbitan esters, propolyene glycol, sorbitan monopalmitate, sorbitan monosterate, sorbitan tristerate, enzyme modified lecithin, hyroxylated lecithins, other like emulsifiers or combinations thereof.

The flavors can be emulsified by any suitable emulsification process, such as mechanical processing, vigorous stirring, intense pressure fluctuations that occur in turbulent flow such as homogenization, sonication, colloid milling and the like.

The present invention provides methods of producing the edible film formulations. In general, the edible film formulations are prepared by forming a base solution that includes at least three types of film forming agents, such as maltodextrins, hydrocolloids and fillers and processing the base solution to form an edible film. Typically, the base solution is prepared by adding an initial mixture of dry ingredients to water that is stirred.

To the base solution, additional ingredients, such as flavor/emulsifier blends, sweeteners, softeners, color, the like or combinations thereof, can be added. In an embodiment, the solution is stirred continuously and heated at a temperature ranging from about 40° C. to about 60° C. The solution then can be dried in any suitable manner, thereby, forming the edible film.

It should be appreciated that any suitable type, number and arrangement of process procedures or steps (i.e. mixing, heating, drying, cooling, addition of ingredients), process parameters (i.e. temperature, pressure, pH, process times) or the like can be utilized.

By way of example and not limitation, the following examples illustrate various embodiments of the edible film formulations of the present invention.

TABLE 2

Antimicrobial Edible Film Formulations

| Ingredient | Example 6 | Example 7 | Example 8 | Example 9 | Example 10 |
|---|---|---|---|---|---|
| Maltodextrin | 25.05 | 47.00 | 31.20 | 36.80 | 21.00 |
| Sodium Alginate | 22.50 | — | 19.00 | — | 12.00 |
| Calcium Alginate | — | 15.15 | — | 11.45 | — |
| Carageenan | — | — | — | — | 12.00 |
| Microcrystalline Cellulose | 25.75 | 9.00 | 18.80 | 13.00 | 20.00 |
| Calcium Carbonate | — | 2.45 | — | — | — |
| Glycerin | 12.25 | 10.00 | 8.00 | — | 9.5 |
| Sorbitol | — | — | — | 6.00 | 1.55 |
| Propylene | — | — | 3.65 | 5.00 | — |

TABLE 2-continued

Antimicrobial Edible Film Formulations

| Ingredient | Example 6 | Example 7 | Example 8 | Example 9 | Example 10 |
|---|---|---|---|---|---|
| Glycol | | | | | |
| Menthol | 1.00 | 0.05 | — | 1.25 | — |
| Eucalyptol | — | 0.05 | — | 1.00 | — |
| Maleic Acid | — | — | — | — | 1.35 |
| Citric Acid | — | — | 1.25 | — | 1.00 |
| Chloro-hexidine | 1.85 | — | — | 1.00 | — |
| Triclosan | — | 1.25 | — | 1.00 | — |
| Flavor | 9.40 | 11.00 | 12.00 | 14.00 | 10.00 |
| High Intensity Sweetener | 1.25 | 1.00 | 1.05 | 1.45 | 1.50 |
| Magnolia Bark Extract | 1.00 | 3.00 | 5.00 | 8.00 | 10.00 |
| Color | 0.05 | 0.05 | 0.05 | 0.05 | 0.10 |
| Total % | 100.00 | 100.00 | 100.00 | 100.00 | 100.00 |

TABLE 3

Antimicrobial Edible Film Formulations

| Ingredient | Example 11 | Example 12 | Example 13 | Example 14 | Example 15 |
|---|---|---|---|---|---|
| Maltodextrin | 35.00 | 30.35 | 28.15 | 25.00 | 30.00 |
| Sodium Alginate | 22.15 | 19.10 | 17.00 | 28.15 | — |
| Carageenan | — | — | — | — | 20.15 |
| Microcrystalline Cellulose | 20.00 | 18.00 | 17.00 | 17.00 | 18.00 |
| Gum Arabic | — | — | 11.00 | — | — |
| Glycerin | 7.30 | 15.00 | 7.30 | 7.30 | 7.30 |
| Flavor | 11.00 | 11.00 | 11.00 | 11.00 | 11.00 |
| Lecithin | 2.00 | 2.00 | 2.00 | 2.00 | 2.00 |
| High Intensity Sweetener | 1.50 | 1.50 | 1.50 | 1.50 | 1.50 |
| Magnolia Bark Extract | 1.00 | 3.00 | 5.00 | 8.00 | 10.0 |
| Color | 0.05 | 0.05 | 0.05 | 0.05 | 0.05 |
| Total % | 100.00 | 100.00 | 100.00 | 100.00 | 100.00 |

In yet another embodiment of the present invention, and effective amount for anti-microbial benefit of Magnolia Bark Extract is present in a confectionery formulation. In an embodiment of the present invention, the amount of Magnolia Bark Extract is present in an amount up to 3% by weight of the confectionery product. In an embodiment of the present invention, the amount of Magnolia Bark Extract is 1% of the weight of the confectionery product. In another embodiment, the Magnolia Bark Extract is present in the amount of 0.01% by weight of the confectionery product. Considering the potency of Magnolia Bark Extract as described in the in vitro studies above, 0.005% by weight of the confectionery product s also effective in bactericidal properties.

Confectionery products for this invention may be hard candies, chewy candies, coated chewy center candies and tabletted candies. By way of example, the hard candy is primarily comprised of corn syrup and sugar, and derives its name from the fact that it contains only 1.0% and 4% moisture. In appearance, these types of candies are solid, but they are actually supercooled liquids, which are far below their melting points. There are different types of hard candies. Glass types are usually clear or made opaque with dyes; and Grained Types, which are always opaque.

The continuous making process of the Deposited Glass Types, with a sugar base are as follows. Corn syrup is spread over a cylinder heated by high pressure steam. Rapid heat exchange causes the water in the syrup to evaporate. The cooked syrup is discharged, colors and flavors are added. They syrup is cooled and deposited onto a stainless steel conveyor. These can be conveyed directly to hoppers which then discharge directly into molds.

The candy is conveyed to batch rollers, which shapes and sizes the batch. The candy enters a former, which shapes the individual pieces into discs, balls, barrels, etc. The present invention can be made into any shape, circles, squares, triangles etc., also into animal shapes or any other novelty molding available. The candy is then cooled, wrapped and packaged.

For Grained Types of candy, water and sugar are the basic components being mixed with other ingredients, and cooked at high temperatures (290° F.-310° F.), causing the water to turn to steam. The product is transferred to a cooling wheel, where it is collected in about 150 pound batches, placed in a pulling machine to aerate the product, and the flavor is added.

The candy is transferred to batch rollers where it is shaped and sized. The candy then enters a former, which shapes the individual pieces. The candy is cooled at a relative humidity of 35% and enters a rotating drum where it is coated with a fine sugar. The candy is then conveyed to the graining room for four hours at 90° F. and 60% humidity. The entrapped air and moisture causes the product to grain.

The present invention can be of a variety of shapes, flavors and sizes. The present invention may contain sugar or may be sugarless.

Flavors used in the present invention may be peppermint oils, citrus oils, arvensis, fruit flavors, spearmint oils and the like.

Colors used in the present invention are colorants are typically known as FD&C dyes and lakes.

By way of example and not limitation, the following examples illustrate various embodiments of the confectionery formulations of the present invention.

TABLE 4

Antimicrobial Candy Formulations

| Ingredient | Example 16 | Example 17 | Example 18 | Example 19 | Example 20 |
|---|---|---|---|---|---|
| Corn Syrup | 45.00 | 43.00 | — | — | 47.00 |
| Sugar | 53.49 | 50.00 | — | — | 47.00 |
| Polyalcohols | — | — | 95.00 | 94.00 | — |
| Flavor | 1.00 | 5.00 | 3.00 | 2.00 | 2.50 |
| Color | 0.50 | 1.00 | 0.60 | 0.80 | 0.50 |
| Magnolia Bark Extract | 0.01 | 1.00 | 1.20 | 3.00 | 3.00 |
| High Intensity Sweetener | — | — | 0.20 | 0.20 | — |
| Total % | 100.00 | 100.00 | 100.00 | 100.00 | 100.00 |

The invention claimed is:
1. A pullulan-free edible film composition comprising:
(a) an effective amount of a film forming agent; and

(b) an effective amount of Magnolia Bark extract, such that the composition provides a concentration of Magnolia Bark extract of about 0.005% to about 0.10% in the oral cavity of a user.

2. The composition of claim 1 wherein the film forming agent comprises a mixture of a maltodextrin, a filler, and a hydrocolloid.

3. The composition of claim 2 wherein the maltodextrin comprises about 5 wt. % to about 60 wt. % of the edible film.

4. The composition of claim 2 wherein the maltodextrin comprises about 20 wt. % to about 40 wt. % of the edible film.

5. The composition of claim 2 wherein the hydrocolloid comprises about 10 wt. % to about 50 wt. % of the edible film.

6. The composition of claim 2 wherein the hydrocolloid comprises about 20 wt. % to about 30 wt. % of the edible film.

7. The composition of claim 2 wherein the filler comprises about 5 wt. % to about 30 wt. % of the edible film.

8. The composition of claim 2 wherein the filler comprises about 15 wt. % to about 25 wt. % of the edible film.

9. The composition of claim 2 wherein the hydrocolloid comprises a material selected from the group consisting of natural gums, biosynthetic gums, natural seaweeds, natural plant extrudates, natural fiber extracts, gelatins, biosynthetic process starches, cellulosic materials, alginates, pectin, and combinations thereof.

10. The composition of claim 2 wherein the hydrocolloid comprises a gum selected from the group consisting of natural seed gum, guar gum, locust gum, tara gum, gum arabic, ghatti gum, agar gum, and xanthan gum.

11. The composition of claim 2 wherein the hydrocolloid comprises sodium alginate or calcium alginate.

12. The composition of claim 2 wherein the hydrocolloid comprises a carrageenan.

13. The composition of claim 2 wherein the filler comprises a food-grade bulk filler selected from the group consisting of microcrystalline cellulose, cellulose polymers, magnesium carbonate, calcium carbonate, ground limestone, silicates, clay, talc, titanium dioxide, calcium phosphates, and combinations thereof.

14. The composition of claim 2 wherein the filler comprises wood.

15. The composition of claim 2 wherein the filler comprises magnesium or aluminum silicate, or combinations thereof.

16. The composition of claim 2 wherein the filler comprises mono-calcium phosphate, di-calcium phosphate, or tri-calcium phosphate, or combinations thereof.

17. The composition of claim 1 wherein the Magnolia Bark Extract comprises about 1 wt % to about 10 wt % of the edible film.

18. The composition of claim 1 wherein the Magnolia Bark Extract comprises about 8 wt % of the edible film.

19. The composition of claim 1 wherein the Magnolia Bark Extract comprises about 5 wt % of the edible film.

20. The composition of claim 1 wherein the Magnolia Bark Extract comprises at least one of Magnolol and honokiol.

21. The composition of claim 1 further comprising an effective amount of a medicament.

22. The composition of claim 21 wherein the medicament comprises an oral cleansing or breath freshening compound selected from the group consisting of pH control agents, inorganic components for tartar or caries control, breath freshening agents, anti-plaque/anti-gingivitis agents, saliva stimulating agents, pharmaceutical agents, nutraceutical agents, vitamins, mineral, and combinations thereof.

23. The composition of claim 21 wherein the medicament comprises urea.

24. The composition of claim 21 wherein the medicament comprises phosphates or fluorides.

25. The composition of claim 21 wherein the medicament comprises zinc gluconate.

26. The composition of claim 21 wherein the medicament comprises chlorohexidine, cetylpyridinium chloride (CPC), or triclosan, or combinations thereof.

27. The composition of claim 21 wherein the medicament comprises a food acid.

28. The composition of claim 27 wherein the food acid comprises an acid selected from the group consisting of citric, lactic, maleic, succinic, ascorbic, adipic, fumaric, tartaric acids, and combinations thereof.

29. The composition of claim 1 further comprising an effective amount of a softening agent.

30. The composition of claim 29 wherein the softening agent comprises about 0 wt % to about 20 wt % of the edible film.

31. The composition of claim 29 wherein the softening agent comprises about 2 wt % to about 10 wt % of the edible film.

32. The composition of claim 29 wherein the softening agent comprises a plasticizer selected from the group consisting of sorbitol, glycerin, polyethylene glycol, propylene glycol, hydrogenated starch hydrolysates, corn syrup, and combinations thereof.

33. The composition of claim 1 further comprising an effective amount of a coloring agent.

34. The composition of claim 1 further comprising an effective amount of a flavoring agent.

35. The composition of claim 34 wherein the flavoring agent comprises about 0.1 wt % to about 20 wt % of the edible film.

36. The composition of claim 34 wherein the flavoring agent comprises about 10 wt % to about 15 wt % of the edible film.

37. The composition of claim 34 wherein the flavoring agent comprises a material selected from the group consisting of essential oils, synthetic flavors, fruit essences, anise, flavor oils with germ killing properties, and combinations thereof.

38. The composition of claim 34 wherein the flavoring agent comprises an oil selected from the group consisting of citrus oil, peppermint oil, spearmint oil, mint oil, clove oil, oil of wintergreen, and combinations thereof.

39. The composition of claim 34 wherein the flavoring agent comprise a material selected from the group consisting of menthol, eucalyptol, thymol, and combinations thereof.

40. The composition of claim 1 further comprising an effective amount of an emulsifying agent.

41. The composition of claim 40 wherein the emulsifying agent comprises a material selected from the group consisting of lecithin, ($C_{10}$-$C_{18}$) fatty acids, mono and diacyl glycerides, ox bile extract, polyglycerol esters, polyethylene sorbitan esters, propylene glycol, sorbitan monopalmitate, sorbitan monosterate, sorbitan tristerate, enzyme modified lecithin, hydroxylated lecithins, and combinations thereof.

42. A method of oral cleansing by applying a pullulan-free edible film to the oral cavity, wherein the edible film comprises:

(a) an effective amount of a film forming agent; and (b) an effective amount of Magnolia Bark Extract such that the composition provides a concentration of Magnolia Park Extract of 0.005%-0.10% in the oral cavity of a user.

43. The method of claim 42 wherein the Magnolia Bark Extract comprises about 1 wt % of the edible film.

44. The method of claim 42 wherein the Magnolia Bark Extract comprises about 5 wt % of the edible film.

45. The method of claim 42 wherein the Magnolia Bark Extract comprises at least one of Magnolol and honokoil.

46. The method of claim 42 wherein the film forming agent comprises a mixture of a maltodextrin, a filler, and a hydrocolloid.

47. The method of claim 46 wherein the maltodextrin comprises about 5 wt. % to about 60 wt. % of the edible film.

48. The method of claim 46 wherein the hydrocolloid comprises about 10 wt. % to about 50 wt. % of the edible film.

49. The method of claim 46 wherein the filler comprises about 5 wt. % to about 30 wt. % of the edible film.

50. The method of claim 46 wherein the hydrocolloid comprises a material selected from the group consisting of natural gums, biosynthetic gums, natural seaweeds, natural plant extrudates, natural fiber extracts, gelatins, biosynthetic process starchs, cellulosic materials, alginates, pectin, and combinations thereof.

51. The method of claim 46 wherein the hydrocolloid comprises a gum selected from the group consisting of natural seed gum, guar gum, locust gum, tara gum, gum arabic, ghatti gum, agar gum, and xanthan gum.

52. The method of claim 46 wherein the hydrocolloid comprises sodium alginate or calcium alginate.

53. The method of claim 46 wherein the hydrocolloid comprises a carrageenan.

54. The method of claim 46 wherein the filler comprises a food-grade bulk filler selected from the group consisting of microcrystalline cellulose, cellulose polymers, magnesium carbonate, calcium carbonate, ground limestone, silicates, clay, talc, titanium dioxide, a calcium phosphates, and combinations thereof.

55. The method of claim 46 wherein the filler comprises wood.

56. The method of claim 46 wherein the filler comprises magnesium or aluminum silicate, or combinations thereof.

57. The method of claim 46 wherein the filler comprises mono-calcium phosphate, di-calcium phosphate, or tri-calcium phosphate, or combinations thereof.

58. The method of claim 42 wherein the edible film further comprises one or more of a medicament, a softening agent, a coloring agent, a flavoring agent, and an emulsifying agent.

59. The method of claim 42 wherein the edible film delivers about 0.1 wt % Magnolia Bark Extract to the oral cavity.

60. The method of claim 42 wherein the edible film delivers about 0.01 wt % Magnolia Bark Extract to the oral cavity.

61. The method of claim 42 wherein the edible film delivers about 0.005 wt % Magnolia Bark Extract to the oral cavity.

62. A method of making a pullulan-free edible film comprising:
(a) forming an aqueous solution that includes a maltodextrin, a hydrocolloid, and a filler;
(b) adding an effective amount of Magnolia Bark Extract such that the film provides a concentration of Magnolia Bark Extract of 0.005-0.10% in the oral cavity of a user; and
(c) drying the aqueous solution to form a dry edible film.

63. The method of claim 62 wherein adding an effective amount of Magnolia Bark Extract comprises adding sufficient Magnolia Bark Extract such that the dry edible film comprises about 1 wt % Magnolia Bark Extract.

64. The method of claim 62 wherein adding Magnolia Bark Extract comprises adding at least one of Magnolol and honokoil.

65. The method of claim 62 wherein forming an aqueous solution comprises adding sufficient maltodextrin such that the dry edible film comprises about 5 wt. % to about 60 wt. % maltodextrin.

66. The method of claim 62 wherein forming an aqueous solution comprises adding sufficient hydrocolloid such that the dry edible film comprises about 10 wt. % to about 50 wt. % hydrocolloid.

67. The method of claim 62 wherein forming an aqueous solution comprises adding sufficient filler such that the dry edible film comprises about 5 wt. % to about 30 wt. % filler.

68. The method of claim 62 wherein forming an aqueous solution further comprises adding one or more of a medicament, a softening agent, a coloring agent, a flavoring agent, and an emulsifying agent.

69. The method of claim 62 further comprising heating the aqueous solution to a temperature of about 40° C. to about 60° C. prior to drying the aqueous solution.

70. A treatment method for reducing the number or activity of bacteria, in the oral cavity comprising the steps of:
(a) providing the edible film composition of claim 1; and
(b) administering to a person in need of the treatment the edible film composition whereby the bacteria in the oral cavity of the person is reduced or inactivated by the treatment.

71. A pullulan-free edible film composition comprising:
(a) an effective amount of a film forming agent; and
(b) an effective amount of Magnolia Bark extract for reducing bacterial concentrations of *Porphyromonas gingivalis* (*P. gingivalis*) and *Fusobactenum nucleatum* (*F. nucleatum*) in the oral cavity of a user, such that the composition provides a concentration of Magnolia Bark extract of about 0.005% to about 0.10% in the oral cavity of the user.

72. The composition of claim 71 wherein the composition provides a minimum inhibitory concentration against *P. gingivalis* at a 0.005% in the oral cavity of the user.

73. The composition of claim 71 wherein the composition provides a minimum inhibitory concentration against *F. nucleatum* at 0.005% in the oral cavity of the user.

* * * * *

UNITED STATES PATENT AND TRADEMARK OFFICE
CERTIFICATE OF CORRECTION

| | | |
|---|---|---|
| PATENT NO. | : 7,347,985 B2 | Page 1 of 1 |
| APPLICATION NO. | : 10/606671 | |
| DATED | : March 25, 2008 | |
| INVENTOR(S) | : James Roy Maxwell et al. | |

It is certified that error appears in the above-identified patent and that said Letters Patent is hereby corrected as shown below:

In the Claims

In column 15, in claim 45, line 2, after "Magnolol and" delete "honokoil" and substitute --honokiol-- in its place.

In column 15, in claim 50, line 5, after "process" delete "starchs" and substitute --starches-- in its place.

In column 15, in claim 54, line 5, before "calcium phosphates" delete "a".

In column 16, in claim 64, line 3, delete "honokoil" and substitute --honokiol-- in its place.

In column 16, in claim 70, line 2, immediately after "activity of bacteria" delete "," (comma).

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,347,985 B2 |
| APPLICATION NO. | : 10/606671 |
| DATED | : March 25, 2008 |
| INVENTOR(S) | : James Roy Maxwell et al. |

It is certified that error appears in the above-identified patent and that said Letters Patent is hereby corrected as shown below:

<u>In the Claims</u>

In column 15, in claim 45, line 10, after "Magnolol and" delete "honokoil" and substitute --honokiol-- in its place.

In column 15, in claim 50, line 25, after "process" delete "starchs" and substitute --starches-- in its place.

In column 15, in claim 54, line 39, before "calcium phosphates" delete "a".

In column 16, in claim 64, line 16, delete "honokoil" and substitute --honokiol-- in its place.

In column 16, in claim 70, line 37, immediately after "activity of bacteria" delete "," (comma).

This certificate supersedes the Certificate of Correction issued October 7, 2008.

Signed and Sealed this

Twenty-first Day of October, 2008

JON W. DUDAS
*Director of the United States Patent and Trademark Office*